US009067072B2

(12) United States Patent
Tahmasian et al.

(10) Patent No.: US 9,067,072 B2
(45) Date of Patent: Jun. 30, 2015

(54) SWITCHABLE DUAL-COIL COMMUNICATION CIRCUITRY FOR EXTENDING COMMUNICATION RANGE IN AN IMPLANTABLE MEDICAL DEVICE SYSTEM

(71) Applicant: Boston Scientific Neuromodulation Corporation, Valencia, CA (US)

(72) Inventors: Samuel Tahmasian, Glendale, CA (US); Tom Stouffer, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 60 days.

(21) Appl. No.: 14/077,704

(22) Filed: Nov. 12, 2013

(65) Prior Publication Data
US 2014/0257432 A1    Sep. 11, 2014

Related U.S. Application Data

(60) Provisional application No. 61/773,422, filed on Mar. 6, 2013.

(51) Int. Cl.
*A61N 1/00* (2006.01)
*A61N 1/36* (2006.01)
*A61N 1/372* (2006.01)

(52) U.S. Cl.
CPC ......... *A61N 1/36125* (2013.01); *A61N 1/37235* (2013.01); *A61N 1/37223* (2013.01)

(58) Field of Classification Search
CPC ........... A61N 1/36125; A61N 1/37223; A61N 1/37235
See application file for complete search history.

(56) References Cited

U.S. PATENT DOCUMENTS

| | | | |
|---|---|---|---|
| 5,480,415 A * | 1/1996 | Cox et al. | 607/32 |
| 5,630,835 A * | 5/1997 | Brownlee | 607/60 |
| 8,010,205 B2 | 8/2011 | Rahman et al. | |
| 8,081,925 B2 | 12/2011 | Parramon et al. | |
| 8,457,756 B2 | 6/2013 | Rahman | |
| 2009/0024179 A1 | 1/2009 | Dronov et al. | |
| 2009/0069869 A1 | 3/2009 | Stouffer et al. | |
| 2012/0095744 A1 | 4/2012 | Rahman et al. | |
| 2012/0101551 A1 | 4/2012 | Aghassian et al. | |

OTHER PUBLICATIONS

U.S. Appl. No. 61/716,662, filed Oct. 22, 2012, Aghassian.

* cited by examiner

*Primary Examiner* — George Manuel
(74) *Attorney, Agent, or Firm* — Lewis & Reese, PLLC

(57) ABSTRACT

Two LC circuits (each with its own coil) are used in either or both of an external controller or an implanted medical device to extend the range at which the two devices can communicate. Only one of the LC circuits (i.e., one of the coils) is used when the device is transmitting, while both LC circuits (i.e., both coils) are used when the device is receiving. When receiving, the LC circuits are preferably connected in series. The series connection of the LC circuits does not affect the resonant frequency, and thus this resonant frequency is the same for both transmission and reception despite the different LC circuits used. Switching circuitry is controlled to disconnect one of the LC circuits when the device is transmitting, and to connect the LC circuits in series during reception.

37 Claims, 12 Drawing Sheets

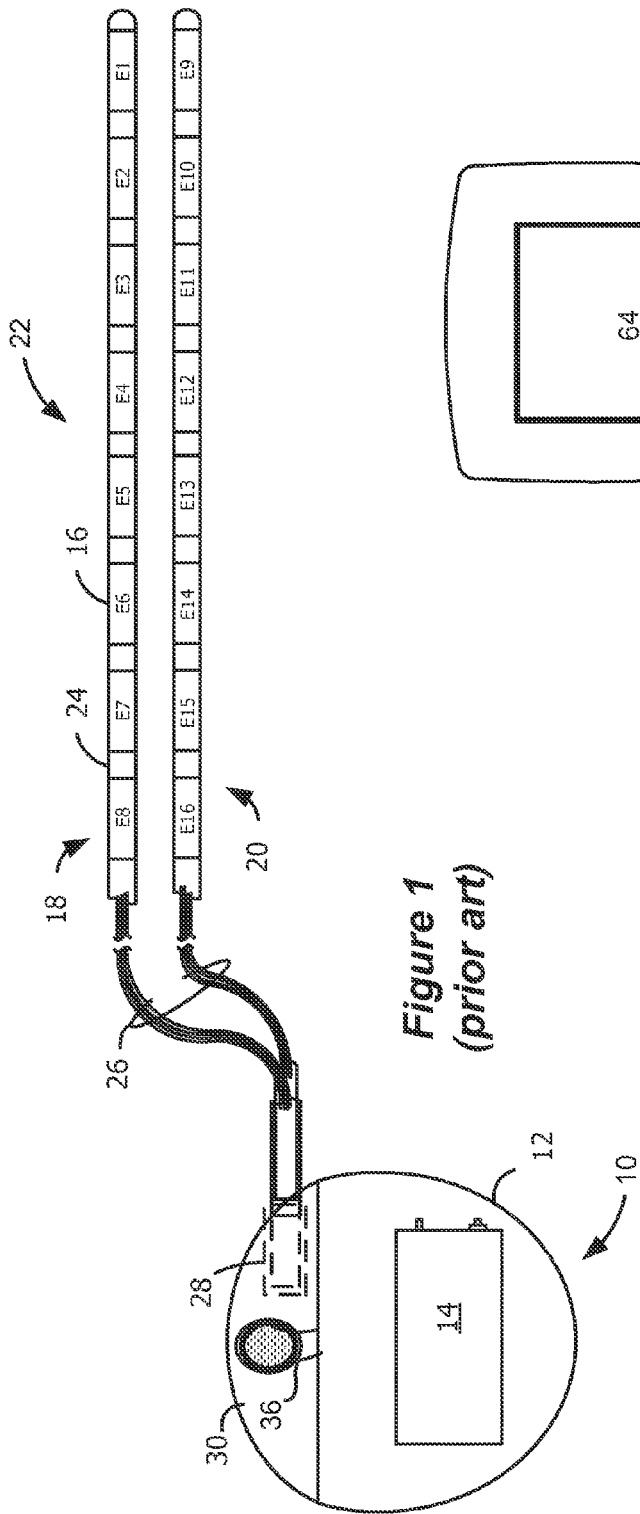
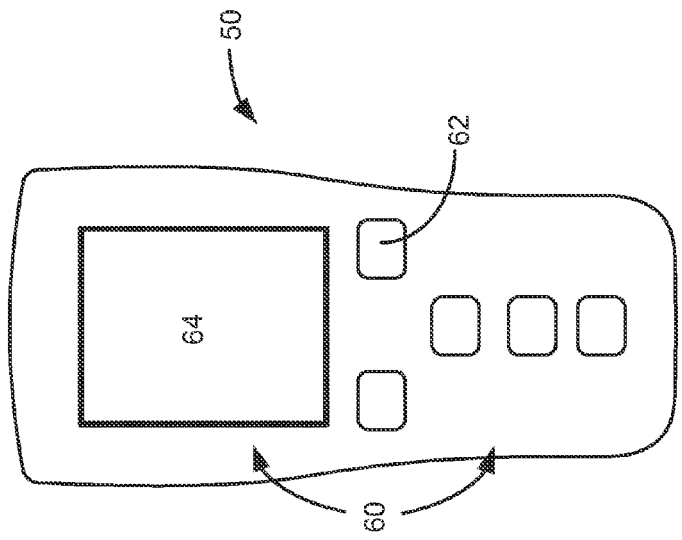
Figure 1
(prior art)
Figure 2
(prior art)

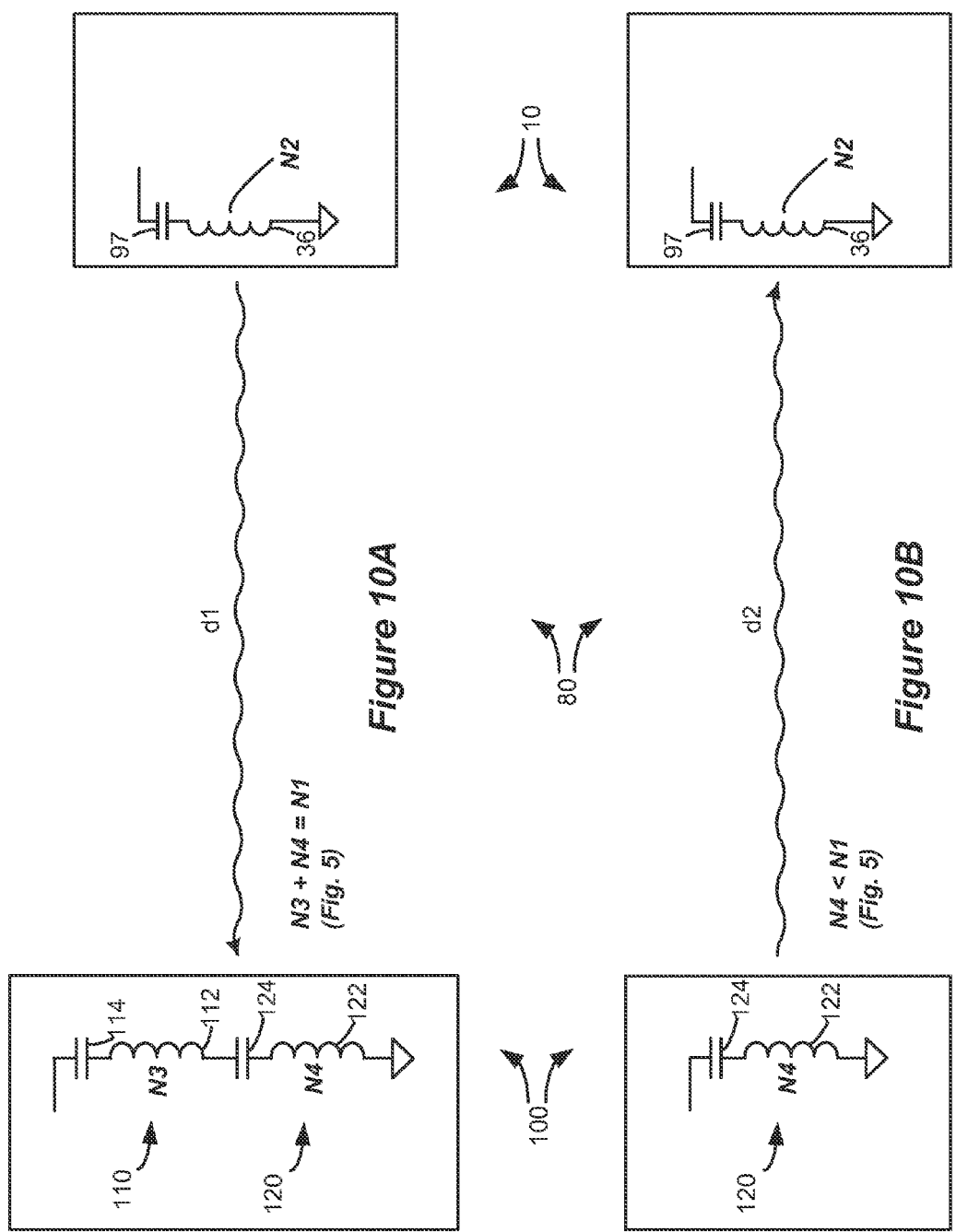

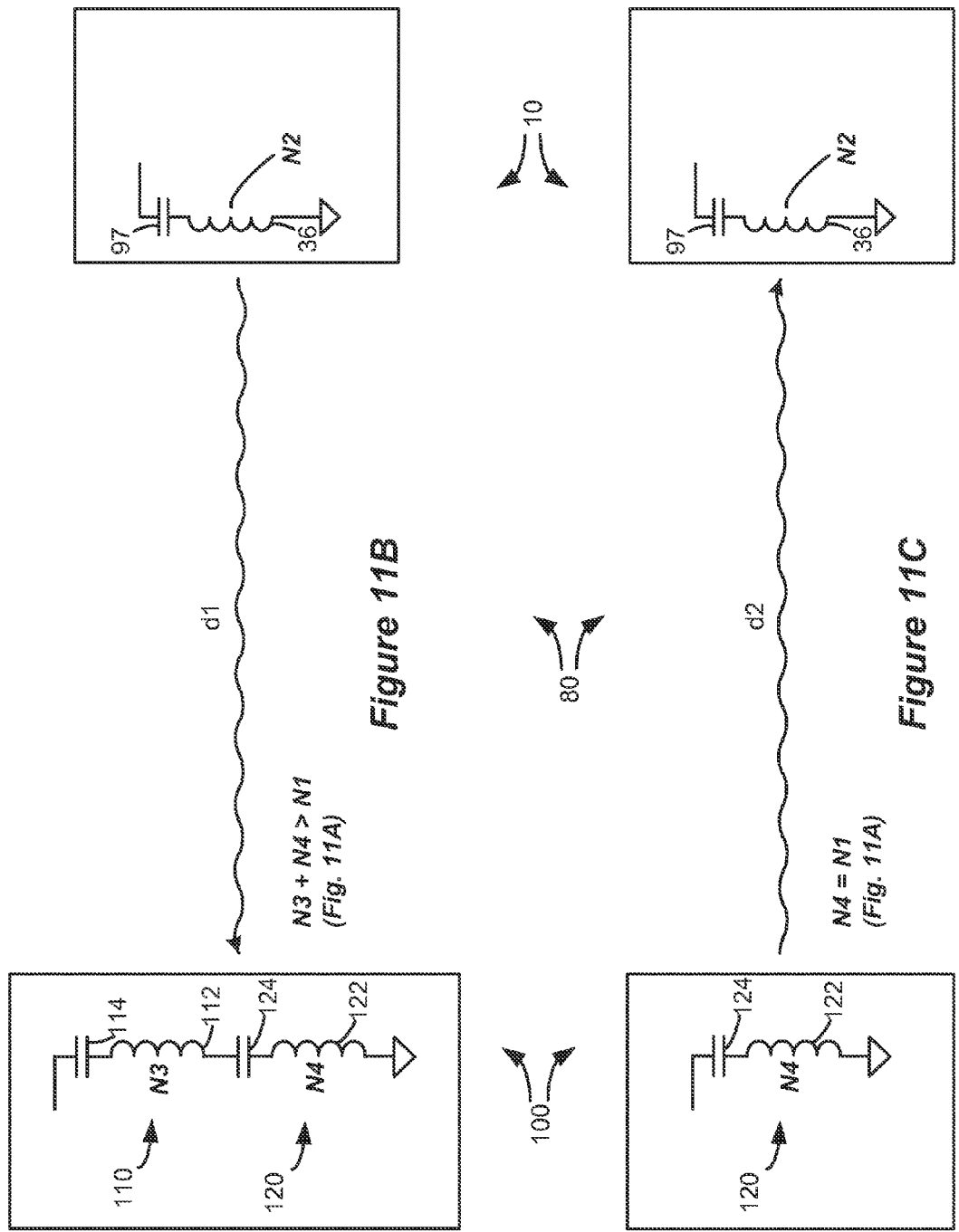

US 9,067,072 B2

SWITCHABLE DUAL-COIL COMMUNICATION CIRCUITRY FOR EXTENDING COMMUNICATION RANGE IN AN IMPLANTABLE MEDICAL DEVICE SYSTEM

CROSS REFERENCE TO RELATED APPLICATIONS

This is a non-provisional of U.S. Provisional Patent Application Ser. No. 61/773,422, filed Mar. 6, 2013, which is incorporated herein by reference, and to which priority is claimed.

FIELD OF THE INVENTION

The present invention relates to an improved implantable medical device system in which either the external controller or the implant contains two coils, one of which is used for transmission, but where both are used in series for reception.

BACKGROUND

Implantable stimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as is disclosed in U.S. Pat. No. 6,516,227. However, the present invention may find applicability in any implantable medical device system.

As shown in FIG. 1, an SCS system typically includes an Implantable Pulse Generator (IPG) 10, which includes a biocompatible device case 12 formed of titanium for example. The case 12 typically holds the circuitry and battery 14 necessary for the IPG to function, although IPGs can also be powered via external RF energy and without a battery. The IPG 10 is coupled to electrodes 16 via one or more electrode leads (two such leads 18 and 20 are shown), such that the electrodes 16 form an electrode array 22. The electrodes 16 are carried on a flexible body 24, which also houses the individual signal wires 26 coupled to each electrode. In the illustrated embodiment, there are eight electrodes on lead 18, labeled E1-E8, and eight electrodes on lead 20, labeled E9-E16, although the number of leads and electrodes is application specific and therefore can vary. The leads 18 and 20 couple to the IPG 100 using lead connectors 28, which are fixed in a header material 30 comprising an epoxy for example. In a SCS application, electrode leads 18 and 20 are typically implantable in a patient's spinal cord.

FIG. 2 shows plan view of an external controller 50 used to communicate with the IPG 10, and FIG. 3 shows both the external controller 50 and IPG 10 in cross section. The external controller 50, such as a hand-held programmer or a clinician's programmer, is used to send data to and receive data from the IPG 10. For example, the external controller 50 can send programming data such as therapy settings to the IPG 10 to dictate the therapy the IPG 10 will provide to the patient. Also, the external controller 50 can act as a receiver of data from the IPG 10, such as various data reporting on the IPG's status.

As shown in FIG. 3, the IPG 10 typically includes an electronic substrate assembly including a printed circuit board (PCB) 34, to which various electronic components 37 are mounted; some of these components are discussed subsequently with respect to FIG. 4. Two coils (antennas) are generally present in the IPG 10: a telemetry coil 36 used to transmit/receive data to/from an external controller 50; and a charging coil 38 for charging or recharging the IPG's battery 14 using an external charger (not shown). The telemetry coil 36 can be mounted within the header 30 of the IPG 10, but is located within the case 12 as shown, and as disclosed in U.S. Patent Application Publication 2011/0112610. The perspective drawing to the right of FIG. 3 shows the telemetry coil 36 in the IPG 10, which generally encompasses an area A2 and comprises a number of turns N2. (The case 12 has been omitted from this drawing to ease viewing of the telemetry coil 36).

The external controller 50, like the IPG 10, also contains a PCB 52 on which electronic components 54 are placed to control operation of the external controller 50; some of these components are also discussed with respect to FIG. 4. The external controller 50 is powered by a battery 56, but could also be powered by plugging it into a wall outlet for example. A telemetry coil 58 is also present in the external controller 50.

The external controller 50 typically comprises a graphical user interface 60 similar to that used for a portable computer, cell phone, or other hand held electronic device. The graphical user interface 60 typically comprises touchable buttons 62 and a display 64, which allows the patient or clinician to operate the external controller 50 to send programs to the IPG 10 and to review any relevant status information that has been reported from the IPG 10.

Wireless data transfer between the IPG 10 and the external controller 50 preferably takes place via magnetic inductive coupling, although a higher radiofrequency link could also be used. To implement indicative coupling functionality, the IPG 10 and the external controller 50 have telemetry coils 36 and 58 as previously mentioned. Either coil can act as the transmitter or the receiver, thus allowing for two-way communication between the two devices. This means of communicating by inductive coupling is transcutaneous, meaning it can occur through the patient's tissue 25.

Referring to FIG. 4, when data originating in the external controller's control circuitry 70 (e.g. a microcontroller) is to be sent from the external controller 50 to the IPG 10, that digital data (TX data) is sent to a modulator 73, where each bit is modulated appropriately in accordance with its data state. For example, if a Frequency Shift Keying (FSK) communications protocol is used, modulator 73 will convert each of the bits to one of two frequencies, f1 or f0, depending on their logic states. f1 may equal 129 kHz, and f0 may equal 121 kHz in one example. This resulting modulated signal can then be amplified 75, and presented to an LC circuit comprising a capacitor 77 and coil 58, which acts as an inductor. The LC circuit is tuned to generally resonate at a center frequency appropriate for the modulated data; for example, values for L and C may be chosen to tune the LC circuit to 125 kHz at the center between f1 and f0. Because LC circuit has some bandwidth, it can generally transmit and receive frequencies close to its center, such as f1 and f0.

The modulated data causes the LC circuit to resonate, and creates an AC modulated magnetic field 80, which is received at the coil 36 in the IPG 10. The IPG 10, like the external controller 50, also comprises an LC circuit comprising a capacitor 97 and coil 36, which again is tuned to the same center frequency of the AC modulated magnetic field (e.g., 125 kHz), and thus capable to receive f1 and f0 which are close to this frequency. The received signal may be amplified 96 and demodulated 94 to recover the original data (RC data). This received data is then sent to the IPG 10's control circuitry 90 (e.g., a microcontroller) for action. If the communication involves adjustment to the therapy the IPG 10 is providing to the patient, the control circuitry 90 communicates relevant instructions to stimulation circuitry 27. As is known, stimulation circuitry 27 includes various current or voltage sources which can be coupled to selected electrodes 16 to provide desired therapy to the patient. Such therapy, typically referred to as a stimulation program, generally specifies various parameters for the stimulation, such as which electrodes 16 are active, whether such electrodes act as anodes (current sources) or cathodes (current sinks), and the duration, frequency, and amplitude of pulses formed at the electrodes. See, e.g., U.S. Patent Application Ser. No. 61/654,603, filed Jun. 1, 2012, for further details concerning stimulation circuitry 27.

Transmission in the other direction—from the IPG 10 to the external controller 50—essentially occurs in the same manner, and similar transmission circuitry (93, 95) in the IPG 10 and reception circuitry (76, 74) in the external controller 50 are present. In both devices, control circuitries 70 and 90 issue a control signal RC/*TX, which informs whether that device is currently transmitting or receiving. For example, when transmitting from the external controller 50, RC/*TX would equal '0' in that device (indicating transmission), while this same control signal would have the opposite state (1') in the IPG 10 (indicating reception). Control signal RC/*TX can also be used to enable or disable various aspects of the communication circuitry. For example, if RC/*TX=0 in a given device, its reception circuitry (e.g., 76 and 74, or 96 and 94) would be disabled, while its transmission circuitry (73 and 75, or 93 and 95) would be enabled.

BRIEF DESCRIPTION OF THE DRAWINGS

FIG. 1 shows an implantable pulse generator (IPG) with an electrode array in accordance with the prior art.

FIG. 2 shows an external controller for communicating with the IPG in accordance with the prior art.

FIGS. 10A and 10B show how the improved dual-coil communication circuitry can be used to extend the two-way communication distance between the external controller and the IPG.

FIGS. 11A-11C show another example of how the improved dual-coil communication circuitry can be used to extend the two-way communication distance between the external controller and the IPG.

DETAILED DESCRIPTION

Figure 4:
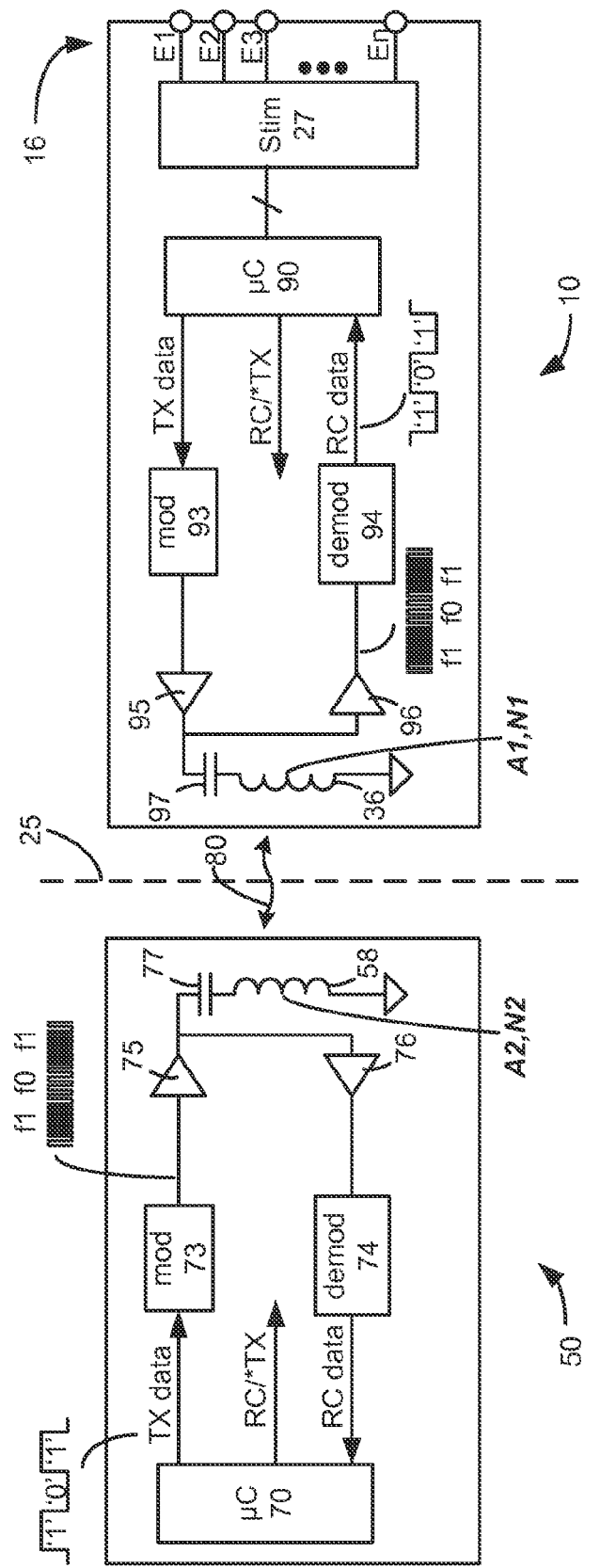
FIG. 4 shows single-coil communication circuitry used in the external controller and the IPG in accordance with the prior art.

The inventors have noted certain drawbacks regarding the communication circuitry used in the external controller 50 and the IPG 10 of FIG. 4. Although it is convenient and simple to use the same telemetry coil for both transmission and reception in either of these devices 10 or 50, it is difficult to optimize a single coil for both reception and transmission in a given device.

Take for example optimization of the number of turns, N, of a transmitter/receiver coil. Transmission is generally improved by decreasing the number of turns of the coil. Reducing the number of turns decreases the coil's resistance, and thus the current through the coil increases for a constant driving voltage such as provided by the transmitting amplifiers 75 and 95 depicted earlier. An increased current increases the strength of the magnetic field produced, and hence increases transmission distance. (Note however that there is a practical limit to how far one can reduce the resistance of a transmit coil. The transmitting amplifier 75 and the battery 56 driving it will generally have low internal resistances, and thus decreasing the number of turns will at some point load this driving circuitry, and decrease the coil's inductance and the resulting strength of the magnetic field).

By contrast, reception is generally improved by increasing the number of turns of the coil. This is because the voltage produced across the coil generally scales with N, and thus a larger number of turns provide a larger voltage signal at the receiving amplifiers 76 and 96, which generally improves the distance at which a receiving device can receive a transmitted signal.

Figure 5:
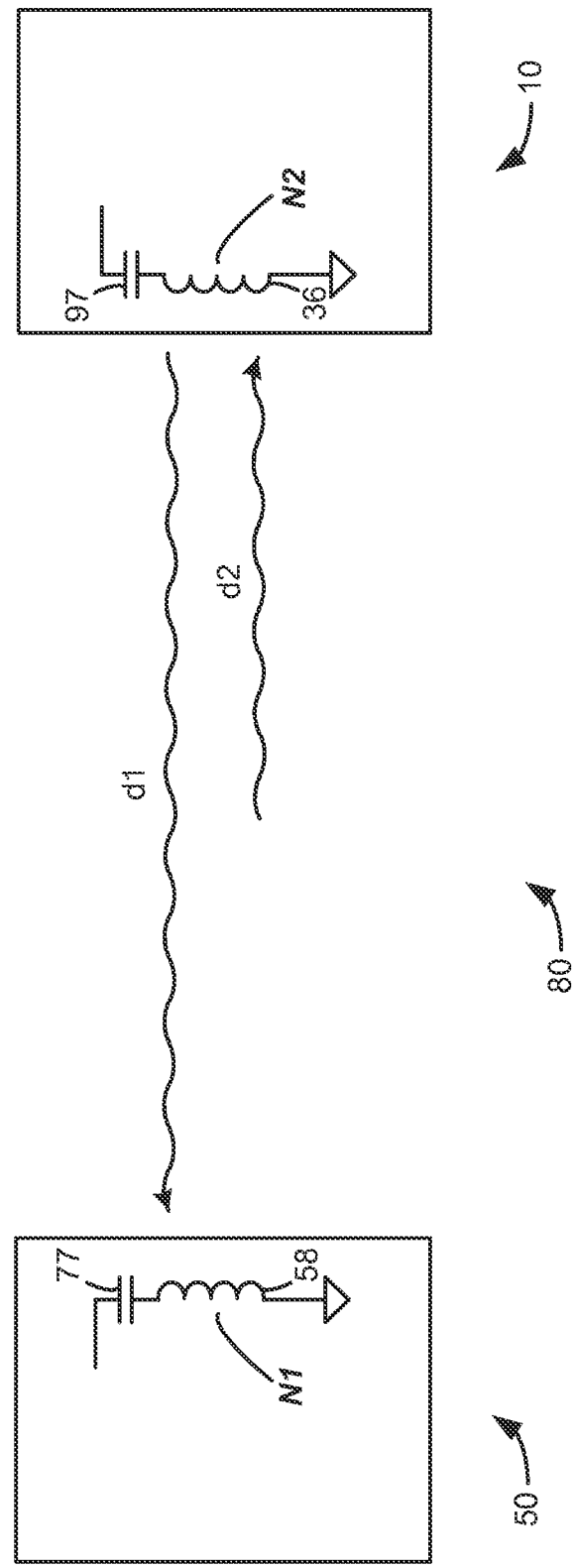
FIG. 5 shows how increasing the two-way communication distance between the external controller and the IPG can be difficult in accordance with the prior art.

An illustration of difficulty of optimization is shown in FIG. 5, in which the telemetry coils 58 and 36 in the external controller 50 and the IPG 10 are assumed to have given number of turns N1 and N2. It may be more difficult to adjust the telemetry coil 36 in the IPG 10 because of space constraints, and therefore the number of turns N2 in the telemetry coil 36 may be fixed and relatively small. A small number of turns N2 would benefit transmission from the IPG 10, but would be poor for IPG reception, as reflected in the differing IPG transmission (d1) and IPG reception (d2) distances depicted. The distance at which the external controller 50 must be placed relative to the IPG 10 for reliable two-way communications is effectively set by the smaller of these distances (d2). This is unfortunate, because under this assumed scenario, IPG transmission distance d1 may be optimal, but any extension of this distance beyond d2 is effectively wasted.

Assuming that the IPG telemetry coil 36 is set and difficult to change, one could attempt to solve this discrepancy in transmission and reception distances by modifying the telemetry coil 58 in the external controller. The external controller 50 generally has more room than does the IPG 10, and therefore, optimization is made more easily on this side of the communication link 80. For example, the number of turns of coil 58 N1 could be reduced, which would strengthen signal transmitted to the IPG 10, effectively increasing IPG reception distance d2. But reducing N1 would also reduce reception at the external controller 50, and hence decrease IPG transmission distance d1. At some point, N1 could be adjusted to the point where d1 and d2 are equal, as discussed in U.S. Patent Application Publication 2012/0095744. But again, this comprises a trade off, and the resulting external controller 50-to-IPG 10 distance may be too small for a given application.

An embodiment of the inventors' solution is to use two LC circuits (each with its own coil) in either or both of the external controller or the IPG. Only one of the LC circuits (i.e., one of the coils) is used when the device is transmitting, while both LC circuits (i.e., both coils) are used when the device is receiving. When receiving, the LC circuits are preferably connected in series. The series connection of the LC circuits does not affect the resonant frequency, and thus this resonant frequency is the same for both transmission and reception despite the different LC circuits used. Switching circuitry is controlled to disconnect one of the LC circuits when the device is transmitting, and to connect the LC circuits in series during reception. As will be seen, this has the benefit of extending the range at which the two devices can communicate.

Figure 6:
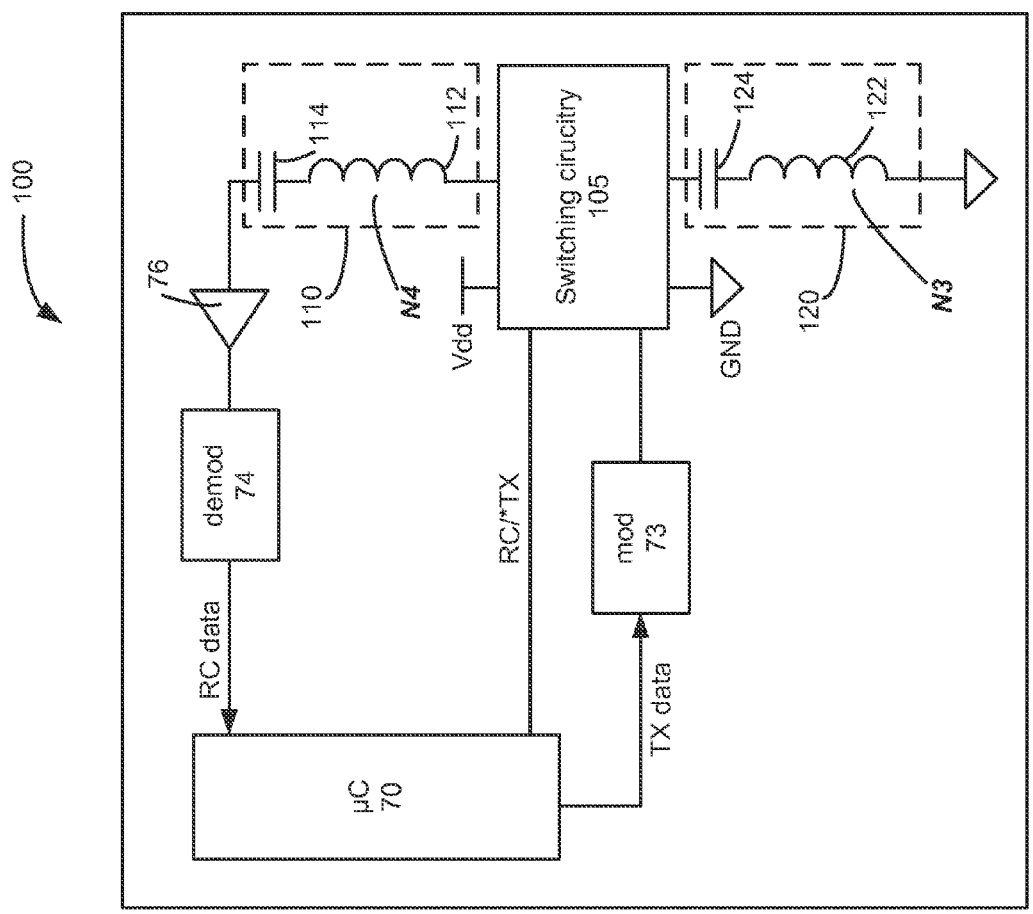
FIG. 6 shows improved dual-coil communication circuitry for use in either the external controller or the IPG, which is illustrated in an improved external controller.

One embodiment of this solution is provided in FIG. 6 in the form of a modified external controller 100 which contains two LC circuits 110 and 120. As just noted, the IPG 10 could be similarly modified, but space constraints in the IPG's case 12 may make adding another LC circuit (and in particular, another coil) difficult in a given application. Therefore, illustration of the technique proceeds initially with focus on modification of the external controller 100, which as an external hand-held device does not suffer from the same space constraints and is thus easier to modify.

As shown, the LC circuits 110 and 120 each comprise an inductor (coil) 112 and 122, and a capacitor 114 and 124. The LC circuits 110 and 120 are tuned to resonate at a frequency desired for communication, for example, 125 kHz as mentioned earlier. Generally, this involves choosing coils 112 and 122 with a desired number of turns (N4 and N3) appropriate for communications, and then choosing capacitors 114 and 124 of appropriate values to match the resulting inductances in accordance with the following equation: $f=1/(2\pi*SQRT(LC))$. Only LC circuit 120 is enabled when the external controller 50 is transmitting, and both LC circuits are enabled and coupled in series when the external device is receiving. Rearranging the above equation, the capacitance of capacitor 124 is chosen as: $C_{124}=1/[L*(2\pi*125\text{ k})^2]$, thus setting the desired frequency (125 kHz) for transmission when only LC circuit 120 is used. The capacitance of capacitor 114, $C_{114}$, is then chosen by solving the following equation: $125\text{ k}=1/(2\pi*SQRT[(L_{122}+L_{112})*[(C_{124}*C_{114})/(C_{124}+C_{114})]])$, thus setting the same frequency (125 kHz) for reception when both LC circuits 110 and 120 are included. Of course, one skilled will realize that certain other circuit parasitics will also be present, and hence $C_{114}$ and $C_{124}$ may vary from ideal values in an actual implementation.

Figure 3:
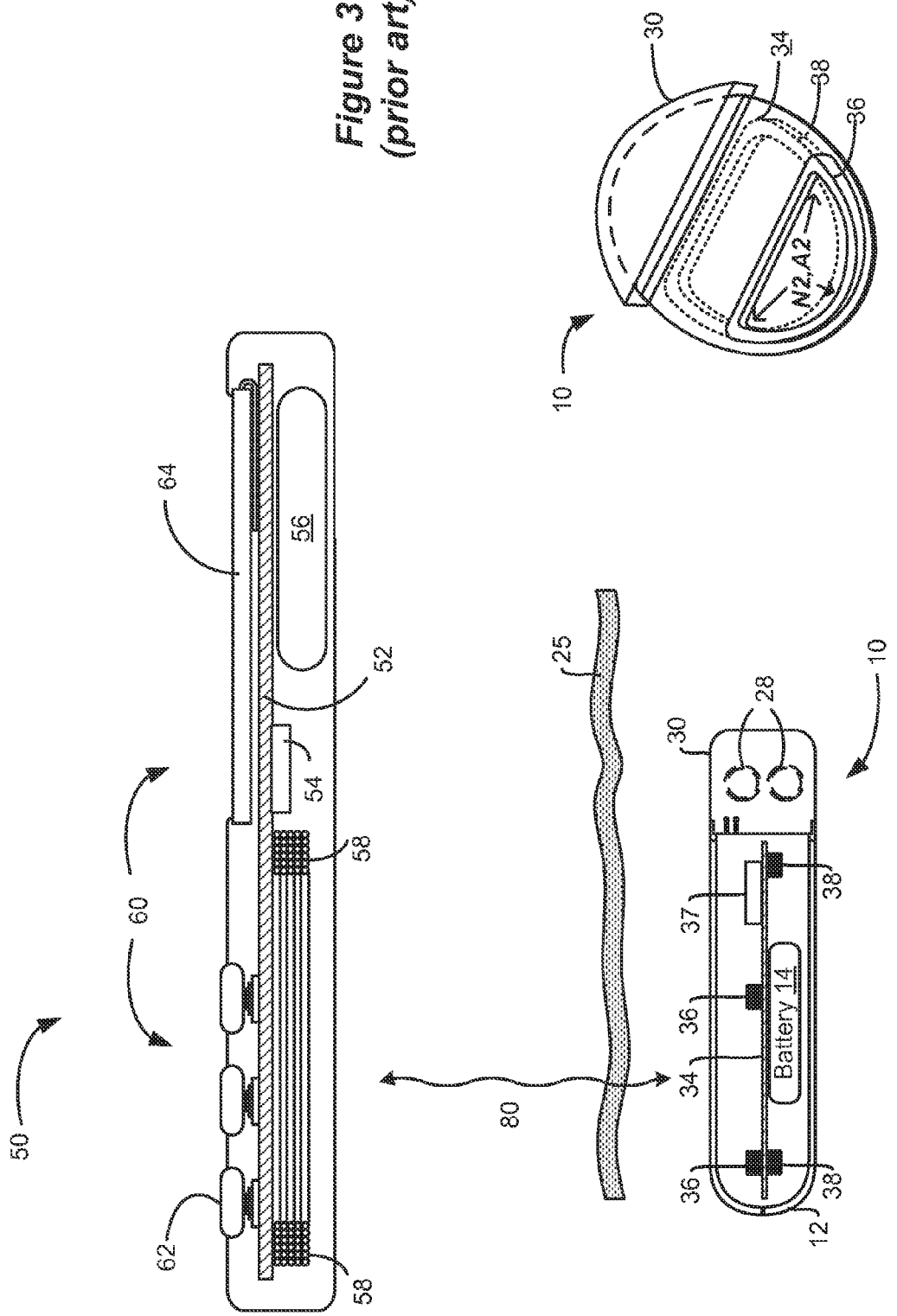
FIG. 3 shows a cross section of the IPG and the external controller, and also shows a perspective view of the IPG with its case removed.

One skilled will realize that there are many ways to make LC circuits 110 and 120 consistent with the above approach. However, in one simulation, the following parameters are used: $L_{122}$=73 µH; $C_{124}$=22.2 nF; N3=27 turns; $L_{112}$=62.5 µH, $C_{114}$=25.9 nF, N4=25 turns). The area of each of the coils is assumed to be about 6 square inches. This simulation assumes that the coils 122 and 112 are formed on the external controller's PCB 52 (FIG. 3) using copper trace widths that are 0.006 inches thick.

The improved external controller 100 contains control circuitry 70, a receiving amplifier 76, a demodulator 74, and a modulator 73, which can be the same as in the prior art external controller 50 of FIG. 4.

Control of the LC circuits 110 and 120 occurs via switching circuitry 105, which is controlled by control signal RC/*TX, which as noted in the Background comprises a control signal that informs the external controller 100 whether it is currently receiving (1') or transmitting (0') data. Control signal RC/*TX, in addition to controlling switching circuitry 105, can also be used as described in the prior art to enable and disable relevant portions of the circuitry, such as the receiving amplifier 76, demodulator 74 and modulator 73. One skilled in the art will recognize that control signal RC/*TX can also comprise a number of control signals, such as separate signals to indicate transmission and reception.

Figure 7:
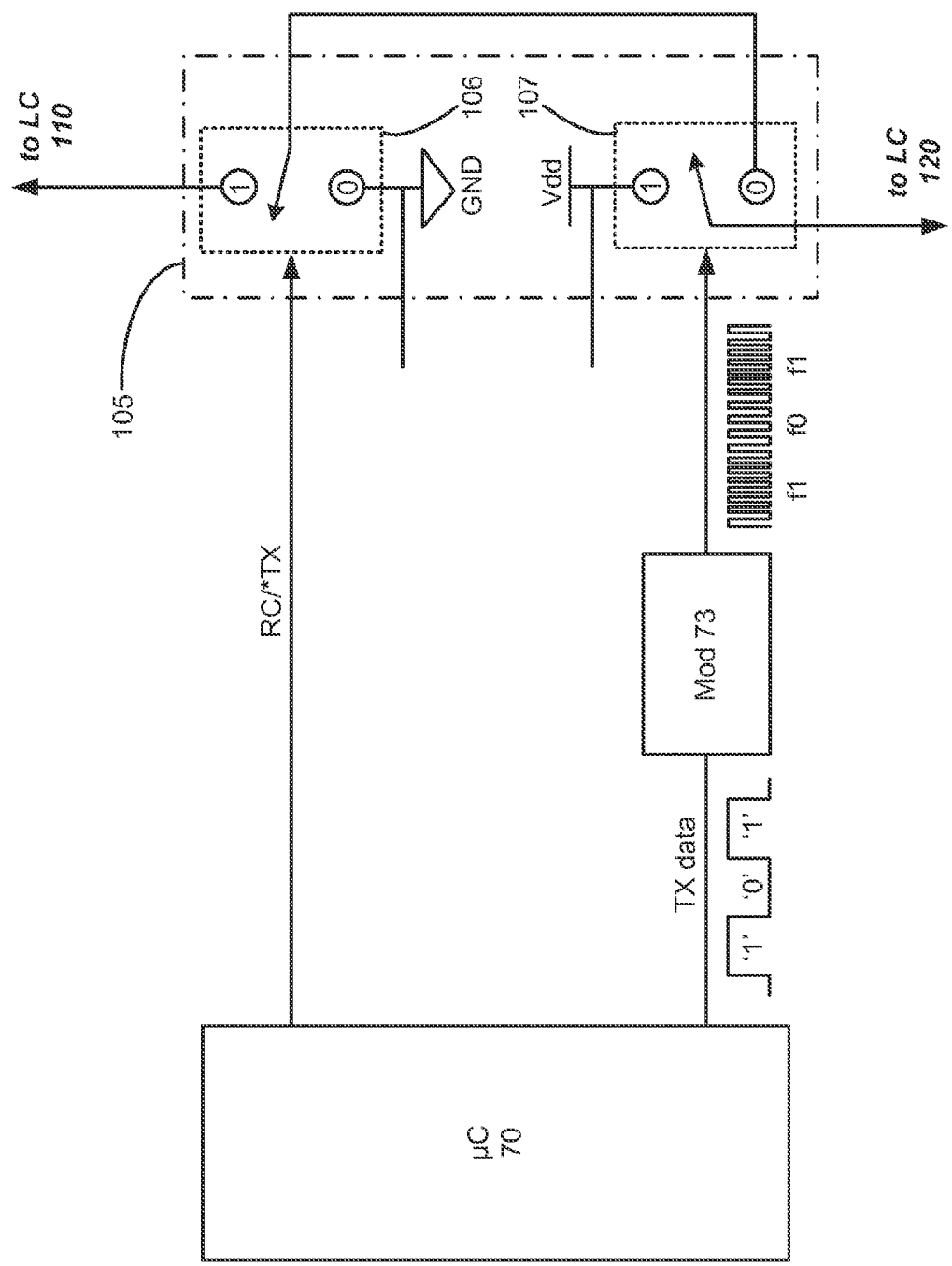
FIG. 7 shows the details of switching circuitry used to controllably select one or both coils in the improved communication circuitry depending whether the external controller is transmitting or receiving.

Internal details of switching circuitry 105 are shown in FIG. 7. Included are two single pole/double throw switches 106 and 107. Switch 106 is controlled by control signal RC/*TX to couple its pole to either LC circuit 110 (1') or to ground (0'). Switch 107 is controlled by the output of modulator 73, which outputs a frequency-modulated square wave in accordance with data being transmitted (TX data). When the square wave is high, the pole of switch 107 couples LC circuit 120 to Vdd; when the square wave is low, LC circuit 120 is connected to the pole of switch 106. Vdd can comprise a voltage of the battery (56; FIG. 2) in the external controller 100, or can comprise a regulated voltage, either of which can comprise a power supply voltage for purposes of this disclosure. Switch circuitry 105 can comprise an analog switch, such Part No. FSA2258, manufactured by Fairchild Semiconductor Corp., or Part No. ADG854, manufactured by Analog Devices, Inc. However, note that switching circuitry 105 can be made in different manners, and using different types and numbers of switches. For example, switching circuitry 105 can be implemented using digital (e.g., CMOS) switches as well.

Figure 8A:
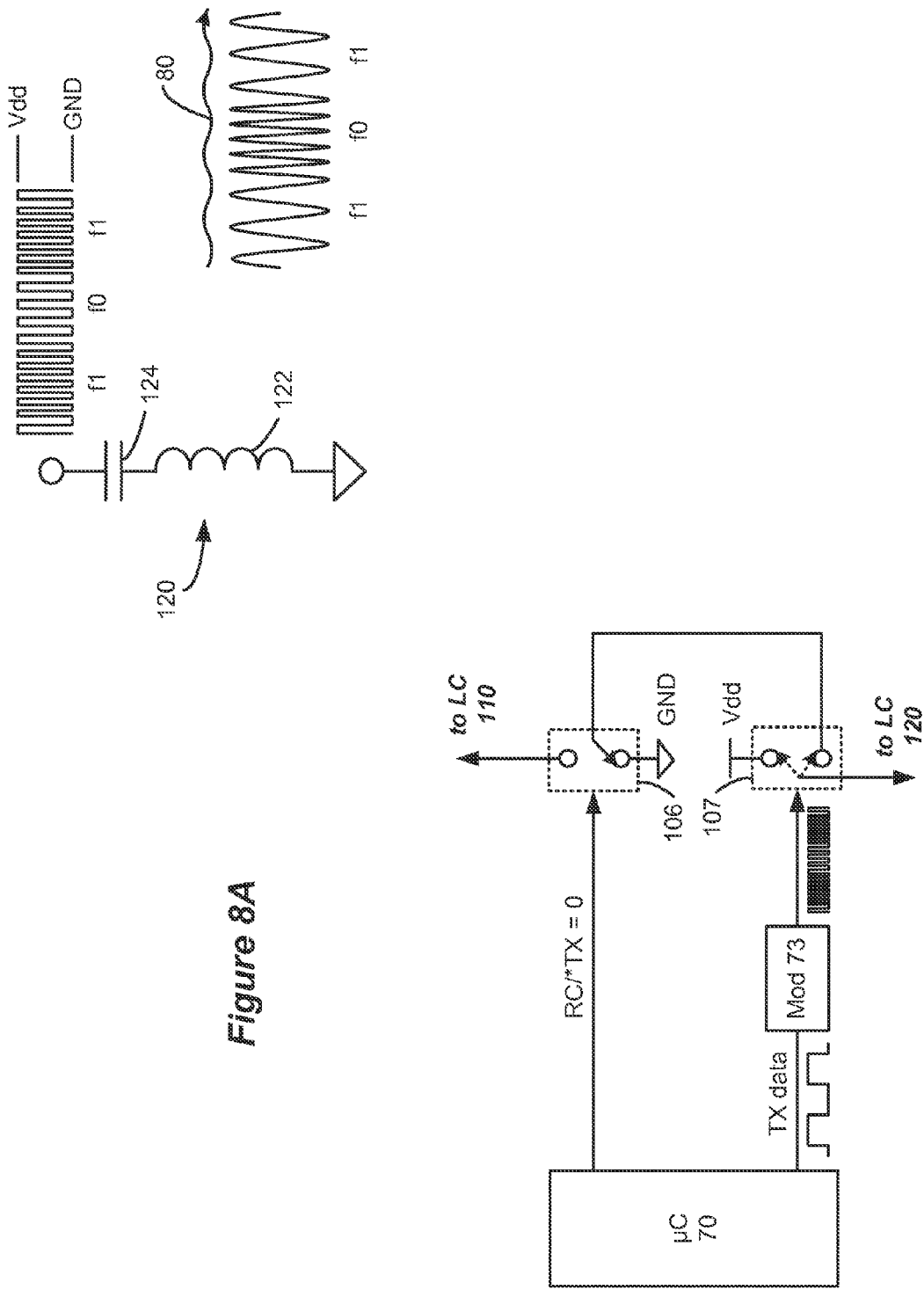
FIGS. 8A and 8B show further details of operation of the improved dual-coil communication circuitry when transmitting and receiving respectively.

FIG. 8A shows relevant aspects of the circuitry in the external controller 100 when configured for transmission, i.e., when RC/*TX=0. The pole in switch 106 is coupled to ground, and thus LC circuit 110 is not connected to the circuit and thus does not participate in transmission. The pole in switch 107 by contrast will alternate in accordance with the frequency of the square wave, coupling that pole to Vdd when high, and to switch 106's pole when low. Because the pole in switch 106 is grounded, in effect LC circuit 120 is coupled between Vdd and ground in accordance with the state of the square wave. (Alternatively, LC circuit 120 could be coupled to any two reference voltages other than Vdd or ground. LC circuit could also be biased to +Vdd when the square wave is high, and to −Vdd when the square wave is low. See, e.g., U.S. Patent Application Publication 2009/0069869). Because the frequency of the square wave generally matches the resonant frequency of LC circuit 120 (e.g. 125 kHz), LC circuit will resonate and broadcast an AC modulated magnetic field 80 to the IPG 10.

Figure 8B:
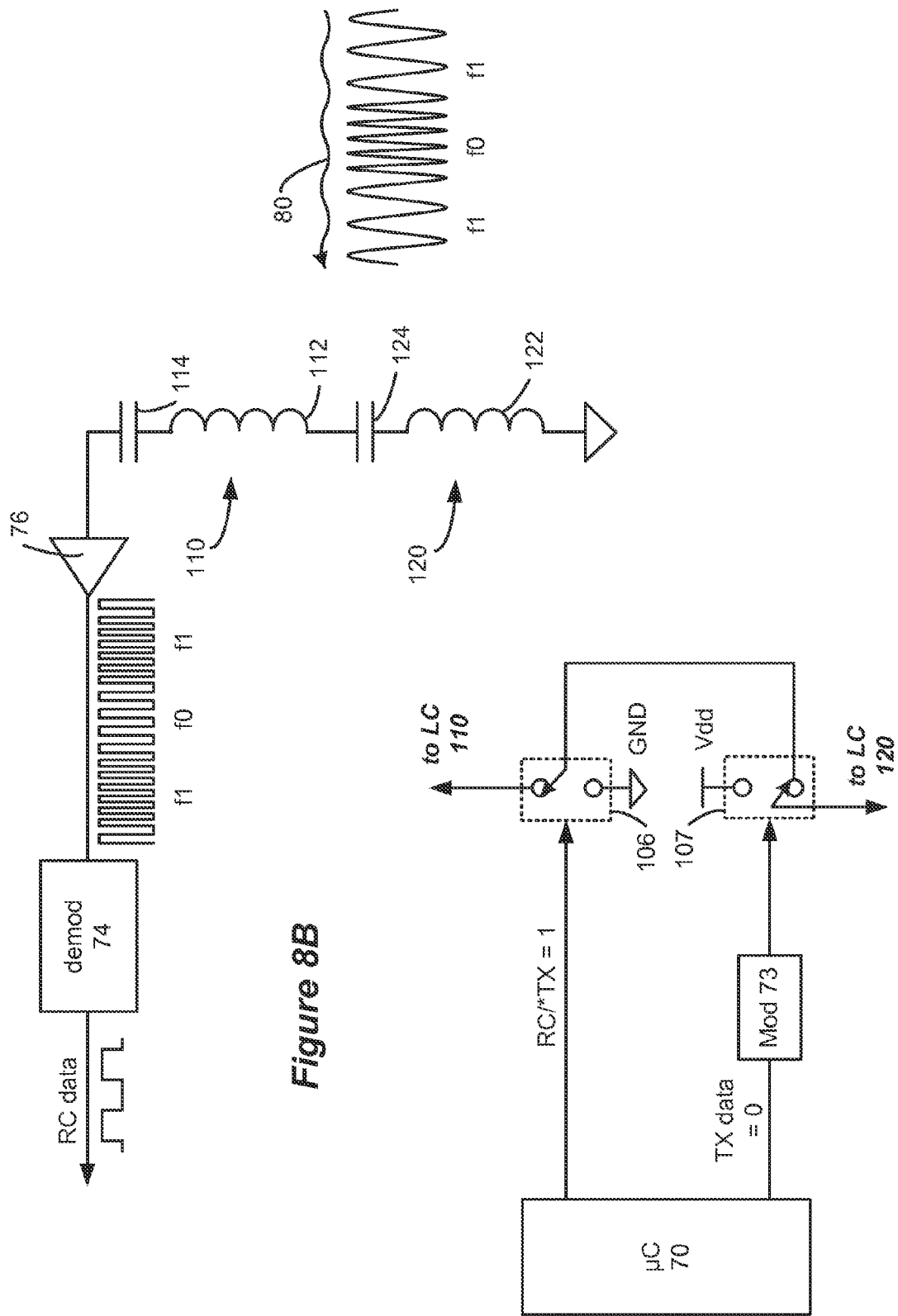

FIG. 8B shows relevant aspects of the circuitry in the external controller 100 when configured for reception, i.e., when RC/*TX=1. The pole in switch 106 is coupled to LC circuit 110, and the pole in switch 107 is coupled to the pole in switch 106. (In switch 107, no transmitted data is present, and thus the control signal for this switch from the modulator 73 set its pole to its '0' setting). Because LC circuit 120 is coupled to the pole of switch 107, this operates to serially connect LC circuits 110 and 112, and hence both are used to receive a transmission from the IPG 10. The transmission is received at both coils 112 and 122, and causes the combined capacitance and inductances in LC circuits 110 and 120 to resonate (e.g. at 125 kHz). Such resonance is amplified (76), and demodulated (74) to recover the received data (RC data).

Figure 9:
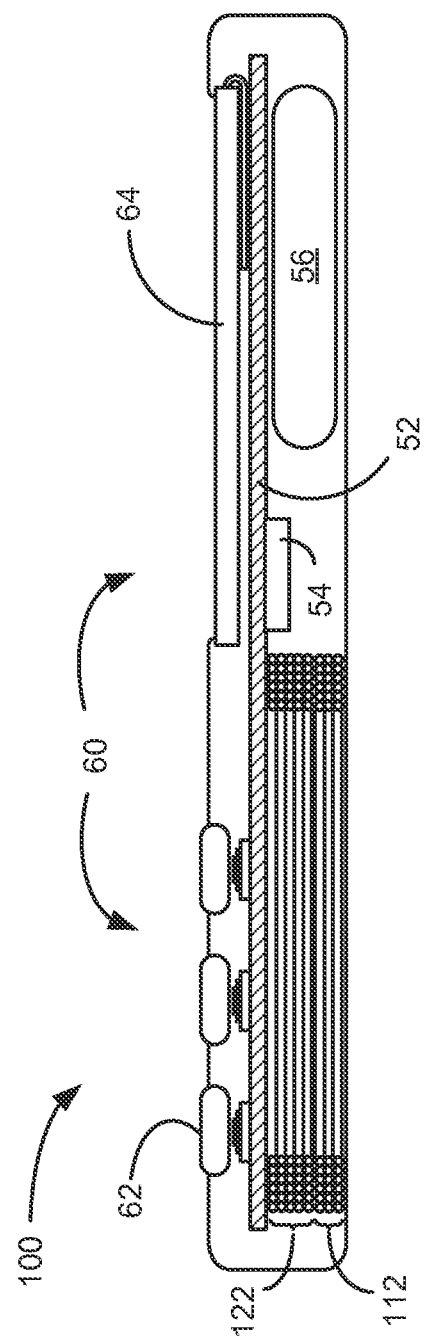
FIG. 9 shows a cross section of the improved external controller including dual coils.

FIG. 9 shows construction of the external controller 100. In this example, the two coils 122 and 112 are wound together on the same bobbin, and essentially stacked on top of each other. The ends of the coils 122 and 112 would be soldered to an appropriate node on the PCB 52 (not shown). It is convenient, but not necessary, to stack the coils 122 and 112 in this manner. The coils 122 and 112 could be located in different places within the housing of the external controller 110, could encompass different areas, and could be made of different types of wire.

FIGS. 10A and 10B show how the dual-coil circuitry of the external controller 100 improves upon the prior art, and in particular the differences in IPG transmission (d1) and reception (d2) distances depicted in FIG. 4 earlier. FIG. 10A shows the IPG's transmission distance d1, i.e., receipt of data at the external controller 100. In this circumstance, the LC circuits 110 and 120 are coupled in series, but the total number of turns provided by each of the coils 112 and 122 (N3+N4) equals the number of turns of the coil 58 (N1) in the prior art external controller 50 (FIG. 5). Therefore, the IPG transmission distance d1 is effectively unchanged. FIG. 10B shows the IPG's reception distance d2, i.e., transmission of data from the external controller 100. In this circumstance, only LC 120 is active. As a result, the total number of turns (N4) is smaller than the number of turns of the coil 58 (N1) in the prior art external controller, which increases the IPG's reception distance d2. Thus, by using the right number of turns N4 in LC circuit 120 and N3 (i.e., N1-N4) in LC circuit 110, the IPG transmission (d1) and reception (d2) distances can be roughly equated as shown. In addition, when one compares FIGS. 5, 10A and 10B, it is noticed that the distance at which the external controller 50 must be placed relative to the IPG 10 for reliable two-way is increased. In effect, the relatively larger transmission distance d1 is persevered, but the reception distance d2 is increased.

Figure 11A:
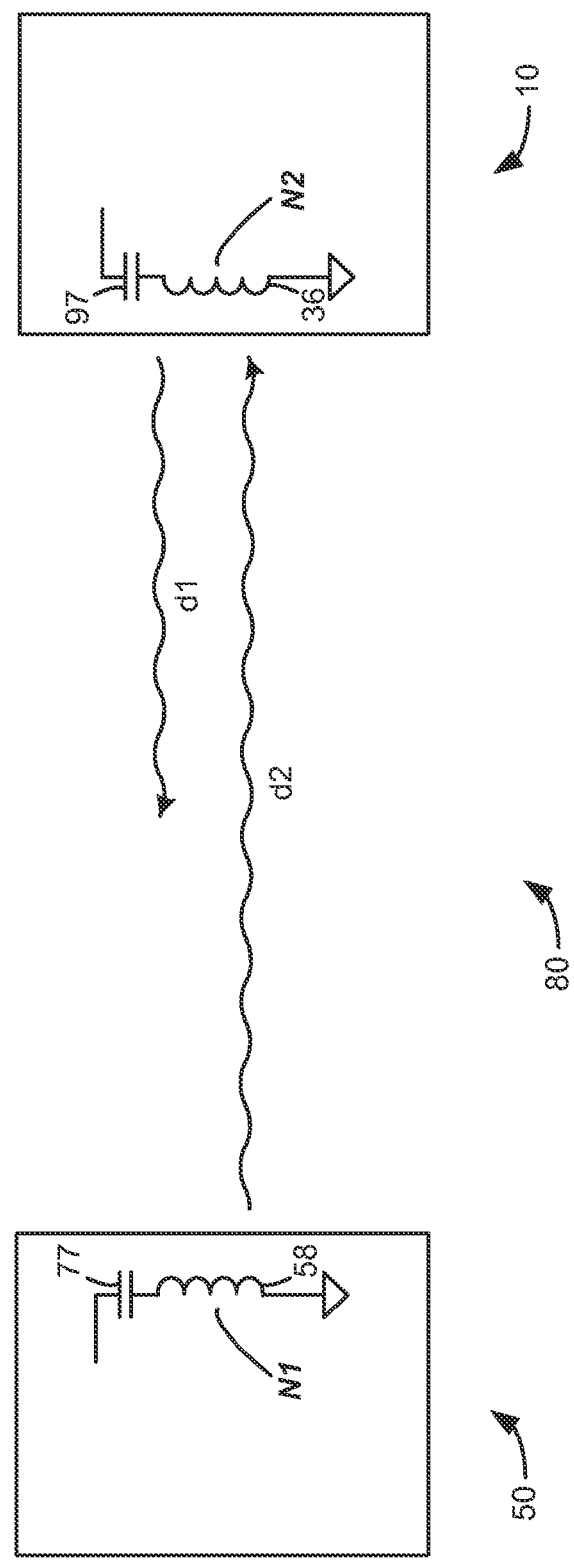

FIGS. 11A-11C show use of the dual-coil circuitry in the external controller 100 to improve upon IPG transmission distance. FIG. 11A illustrates communications between the prior art external controller 50 and the IPG 10, but illustrates the opposite problem to that shown in FIG. 5; namely, in FIG. 11A, the IPG transmission distance d1 is smaller than the IPG reception distance d2. FIGS. 11B and 11C show use of the improved external controller 100 to solve this problem. IPG reception distance d2 (FIG. 11C) is left is unaffected by using an LC circuit 120 having the same number of windings (N4) as was used in the prior art external controller (N1; FIG. 11A). However, IPG transmission distance d1 is increased (FIG. 11B) by including the additional windings N3 in LC circuit 120 (N3+N4>N1) to improve reception of the signal at the external controller 100.

To this point, it has been assumed that the coils 112 and 122 in LC circuits 110 and 120 are essentially equal in area and in composition (i.e., composed of the same type of wire), but this does not have to be the case. For example, in FIG. 11B, coil 112 in LC circuit 110 of FIG. 11B could be made larger in area A than coil 122 in LC circuit 120. The received signal voltage at a receiving coil varies with area as well as with the number of turns, and therefore an increased area for coil 112 would also increase the IPG's transmission distance d1 in FIG. 11B. In short, area A comprises another parameter which can be varied in the formation of coils 112 and 122.

Additionally, the composition of the wires in the coils 112 and 122 can also be different. For example, wire resistance is generally less critical in a receiving coil. Therefore, coil 112 might be made of thinner (i.e., more resistive) wire, thus allowing more turns to be made in a particular volume provided for this coil. The additional number of turns of such thinner wire would assist in improving the IPG transmission distance d1, without affecting the IPG reception distance d2 because coil 122 can continue to be made of thicker (i.e., less resistive) wire. Wire composition is thus also another parameter which can be varied in the formation of coils 112 and 122.

As mentioned earlier, use of the improved dual-coil circuitry has been illustrated with respect to its use in the external controller, but an improved IPG could also use such circuitry. In fact, the improved dual-coil circuitry could be used in both the external controller and the IPG, which after optimization would lead to devices requiring less coil turns, thus saving space in both devices.

Although the LC circuits 110 and 120 are shown as connecting the coils and capacitors in series, one skilled in the art will recognize that they can also be connected in parallel.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A communications device useable in an implantable medical device system, comprising:
   a first resonant circuit having an inductive coil and a capacitor connected in series;
   a second resonant circuit having an inductive coil and a capacitor connected in series; and
   control circuitry configured to issue at least one control signal indicating whether the communications device is to transmit data or receive data,
   wherein the at least one control signal enables only the first resonant circuit to transmit data, and wherein the at least one control signal enables both the first and second resonant circuits to receive data.

2. The communications device of claim 1, wherein the coils in the first and second resonant circuits are stacked.

3. The communications device of claim 1, wherein the coils in the first and second resonant circuits have different areas.

4. The communications device of claim 1, wherein the coils in the first and second resonant circuits comprise different types of wire.

5. The communications device of claim 1, wherein the coils in the first and second resonant circuits comprise different numbers of turns.

6. The communications device of claim 1, wherein the communications device comprises an implantable medical device in the implantable medical device system for communicating with an external controller in the implantable medical device system.

7. The communications device of claim 6, wherein the implantable medical device comprises an implantable neurostimulator device.

8. The communications device of claim 1, wherein the communications device comprises an external controller in the implantable medical device system for communicating with an implantable medical device in the implantable medical device system.

9. The communications device of claim 1, wherein the first resonant circuit transmits data at a first frequency, and wherein both the first and second resonant circuits receive data at the first frequency.

10. The communications device of claim 9, wherein the first frequency comprises a center frequency of a communications protocol.

11. The communications device of claim 10, wherein the communications protocol comprises a Frequency Shift Keying (FSK) protocol.

12. The communications device of claim 1, wherein the at least one control signal enables both the first and second resonant circuits to receive data by coupling the first and second resonant circuits in series.

13. A communications device useable in an implantable medical device system, comprising:
    a first resonant circuit having an inductive coil and a capacitor connected in series;
    a second resonant circuit having an inductive coil and a capacitor connected in series;
    control circuitry configured to issue at least one control signal indicating whether the communications device is to transmit data or receive data; and
    switching circuitry controlled by the at least one control signal, wherein the switching circuitry is configured to use only the first resonant circuit to transmit data, and wherein the switching circuitry is configured to couple the first and second resonant circuits to receive data.

14. The communications device of claim 13, wherein the coils in the first and second resonant circuits are stacked.

15. The communications device of claim 13, wherein the coils in the first and second resonant circuits have different areas.

16. The communications device of claim 13, wherein the coils in the first and second resonant comprise different types of wire.

17. The communications device of claim 13, wherein the coils in the first and second resonant circuits comprise different numbers of turns.

18. The communications device of claim 13, wherein the communications device comprises an implantable medical device in the implantable medical device system for communicating with an external controller in the implantable medical device system.

19. The communications device of claim 13, wherein the communications device comprises an external controller in the implantable medical device system for communicating with an implantable medical device in the implantable medical device system.

20. The communications device of claim 13, wherein the first resonant circuit transmits data at a first frequency, and wherein both the first and second resonant circuits receive data at the first frequency.

21. The communications device of claim 20, wherein the first frequency comprises a center frequency of a communications protocol.

22. The communications device of claim 21, wherein the communications protocol comprises a Frequency Shift Keying (FSK) protocol.

23. The communications device of claim 13, wherein the switching circuitry is configured to couple the first and second resonant circuits in series to receive data.

24. The communications device of claim 13, wherein the transmit data is modulated, and wherein the switching circuitry is configured to switch the first resonant circuit between two reference voltages in accordance with the modulated transmit data.

25. The communications device of claim 24, wherein the two reference voltages comprise a power supply voltage or ground.

26. The communications device of claim 24, further comprising demodulation circuitry for demodulating the received data, wherein the demodulation circuitry is coupled to the second resonant circuit.

27. An external controller for transmitting data to and receiving data from an implantable medical device, comprising:
    a first resonant circuit comprising a first capacitor and a first coil;
    a second resonant circuit comprising a second capacitor and a second coil;
    control circuitry configured to issue digital data to be transmitted and to receive digital data from the implantable medical device, and configured to issue at least one control signal indicating whether the external controller is to transmit data to or to receive data from the implantable medical device; and
    switching circuitry controlled by the at least one control signal, wherein the switching circuitry is configured to use only the first resonant circuit to transmit data at a first frequency, and wherein the switching circuitry is configured to connect the first and second resonant circuits in series to receive data at the first frequency.

28. The external controller of claim 27, wherein the first and second coils are stacked.

29. The external controller of claim 27, wherein the first and second coils have different areas.

30. The external controller of claim 27, wherein the first and second coils comprise different types of wire.

31. The external controller of claim 27, wherein the first and second coils comprise different numbers of turns.

32. The external controller of claim 27, wherein the first coil and the first capacitor are connected in series, and wherein the second coil and the second capacitor are connected in series.

33. The external controller of claim 27, wherein the first frequency comprises a center frequency of a communications protocol.

34. The external controller of claim 33, wherein the communications protocol comprises a Frequency Shift Keying (FSK) protocol.

35. The external controller of claim 27, further comprising a modulator configured to modulate the digital data to be transmitted, wherein the switching circuitry is configured to switch the first resonant circuit between two reference voltages in accordance with the modulated transmit data.

36. The external controller of claim 35, wherein the two reference voltages comprise a power supply voltage or ground.

37. The external controller of claim 35, further comprising a demodulator configured to demodulate the received data to form the received digital data, wherein the demodulator is coupled to the second resonant circuit.

* * * * *